United States Patent
Bosch et al.

(10) Patent No.: US 7,790,039 B2
(45) Date of Patent: Sep. 7, 2010

(54) TANGENTIAL FLOW FILTRATION DEVICES AND METHODS FOR STEM CELL ENRICHMENT

(75) Inventors: Marnix L. Bosch, Medina, WA (US); Patricia A. Lodge, Everett, WA (US); Julie Anna McEarchern, Mill Creek, WA (US); Alton L. Boynton, Kingston, WA (US); Paul G. Hugenholtz, AA Oosterbeek (NL)

(73) Assignee: Northwest Biotherapeutics, Inc., Bethesda, MD (US)

( * ) Notice: Subject to any disclaimer, the term of this patent is extended or adjusted under 35 U.S.C. 154(b) by 1368 days.

(21) Appl. No.: 10/992,154

(22) Filed: Nov. 18, 2004

(65) Prior Publication Data
US 2005/0189297 A1    Sep. 1, 2005

Related U.S. Application Data

(60) Provisional application No. 60/524,511, filed on Nov. 24, 2003.

(51) Int. Cl.
*B01D 61/00* (2006.01)
*B01D 11/00* (2006.01)
*C12N 5/00* (2006.01)
*A01N 1/02* (2006.01)

(52) U.S. Cl. .............. 210/645; 210/650; 210/651; 435/2; 435/297.4; 435/372; 435/373; 435/172.1; 424/529

(58) Field of Classification Search .............. 210/650, 210/651, 645; 435/372, 373, 366, 172.1, 435/172.3, 240.1, 2, 297.4, 272, 172, 3; 424/529
See application file for complete search history.

(56) References Cited

U.S. PATENT DOCUMENTS

| | | | | |
|---|---|---|---|---|
| 4,240,398 A | * | 12/1980 | Lindop | 126/25 R |
| 4,420,398 A | | 12/1983 | Castino | |
| 4,644,056 A | | 2/1987 | Kothe et al. | |
| 4,722,902 A | * | 2/1988 | Harm et al. | 435/297.4 |
| 5,192,553 A | * | 3/1993 | Boyse et al. | 424/529 |
| 5,423,738 A | | 6/1995 | Robinson et al. | |
| 5,843,780 A | * | 12/1998 | Thomson | 435/363 |
| 5,846,427 A | * | 12/1998 | Kessler et al. | 210/645 |

(Continued)

FOREIGN PATENT DOCUMENTS

EP    0 208 450    1/1987

(Continued)

OTHER PUBLICATIONS

Assmus, B. et al., "Transplantation of progenitor cells and regeneration enhancement in acute myocardial infarction (TOPCARE-AMI)," *Circulation*, 106:3009-3017 (Dec. 10, 2002).

(Continued)

*Primary Examiner*—Ana M Fortuna
(74) *Attorney, Agent, or Firm*—Christensen O'Connor Johnson Kindness PLLC

(57) ABSTRACT

The present invention provides methods for enriching a heterogeneous mixture of bone marrow or blood constituents for stem cells by removal of non-stem cell constituents comprising separation of the non-stem cell constituents using a tangential flow filtration device.

27 Claims, 3 Drawing Sheets

U.S. PATENT DOCUMENTS

| | | | |
|---|---|---|---|
| 5,948,441 | A | 9/1999 | Lenk et al. |
| 6,140,040 | A * | 10/2000 | Palm et al. ..................... 435/2 |
| 6,183,640 | B1 * | 2/2001 | Wang .................... 210/500.41 |
| 6,313,285 | B1 | 11/2001 | Butler et al. |
| 6,455,306 | B1 * | 9/2002 | Goldstein et al. ........... 435/372 |
| 6,544,506 | B2 * | 4/2003 | Reisner ...................... 424/93.1 |
| 6,565,427 | B2 * | 5/2003 | Kuwabara et al. ............. 453/21 |
| 6,949,355 | B2 * | 9/2005 | Yamanishi et al. ............. 435/34 |
| 6,984,379 | B1 * | 1/2006 | Kohn et al. .............. 424/93.21 |
| 7,002,027 | B1 * | 2/2006 | Engler et al. ................ 552/549 |
| 2003/0134416 | A1 * | 7/2003 | Yamanishi et al. .......... 435/372 |

FOREIGN PATENT DOCUMENTS

| | | |
|---|---|---|
| WO | WO 85/03011 | 7/1985 |
| WO | WO 2004/000444 A1 | 12/2003 |
| WO | WO 2004/076651 A2 | 9/2004 |

OTHER PUBLICATIONS

Badorff, C. et al., "Transdifferentiation of blood-derived human adult endothelial progenitor cells into functionally active cardiomyocytes," *Circulation*, 107:1024-1032 (Feb. 25, 2003).

Becker, S. et al., "Colony-stimulating factor-induced monocyte survival and differentiation into macrophages in serum-free cultures," *J. Immunol.*, 139:3703-3709 (Dec. 1, 1987).

Britten, M.B. et al., "Infarct remodeling after intracoronary progenitor cell treatment in patients with acute myocardial infarction (TOPCARE-AMI): Mechanistic insights from serial contrast-enhanced magnetic resonance imaging," *Circulation*, 108:2212-2218 (Nov. 4, 2003).

Deliliers, G. et al., "Harvesting of autologous blood stem cells after a mobilising regimen with low-dose cyclophosphamide," *Leuk. Lymphoma*, 43:1957-1960 (Oct. 2002).

Denning-Kendal, P.A. et al. "Different behaviour of fresh and cultured CD34+ cells during immunomagnetic separation," *Br. J. Haematol.*, 105:780-785 (Jun. 1999).

Genovesi, C., "Several uses for tangential-flow filtration in the pharmaceutical industry," *J. Parenter. Sci. Technol.*, 37:81-86 (May-Jun. 1983).

Gill, M. et al., "Vascular trauma induces rapid but transient mobilization of VEGFR2$^+$AC133$^+$ endothelial precursor cells," *Circ. Res.*, 88:167-174 (Feb. 2, 2001).

Havemann, K. et al., "In vitro transformation of monocytes and dendritic cells into endothelial like cells," in *Novel Angiogenic Mechanisms: Role of Circulating Progenitor Endothelial Cells*, pp. 47-57, Nicanor I. Moldovan eds., 2003.

Laham, R. and Oettgen, P., "Bone marrow transplantation for the heart: fact or fiction?" *Lancet*, 361:11-12 (Jan. 4, 2003).

Nicholson, G. et al., "Induction of osteoclasts from CD14-positive human peripheral blood mononuclear cells by receptor activator of nuclear factor κB ligand (RANKL)," *Clin. Sci. (Lond.)*, 99:133-140 (Aug. 2000).

Orlic, D. et al., "Bone marrow cells regenerate infarcted myocardium," *Nature*, 410:701-705 (Apr. 5, 2001).

Peichev, M. et al., "Expression of VEGFR-2 and AC133 by circulating human CD34+ cells identifies a population of functional endothelial precursors," *Blood*, 95:952-958 (Feb. 1, 2000).

Perin, E. et al., "Transendocardial, autologous bone marrow cell transplantation for severe, chronic ischemic heart failure," *Circulation*, 107:2294-2302 (May 13, 2003).

Pujol, B. et al., "Endothelial-like cells derived from human CD14 positive monocytes," *Differentiation*, 65:287-300 (Jun. 2000).

Quirk, A and Woodrow, J. "Investigation of the parameters affecting the separation of bacterial enzymes from cell debris by tangential flow filtration," *Enzyme Microb. Technol.*, 6:201-206 (May 1984).

Radlett, P.J., "The concentration of mammalian cells in a tangential flow filtration unit," *Appl. Chem. Biotechnol.*, 22:495-499 (1972).

Rehman, J. et al., "Peripheral blood 'Endothelial Progenitor Cells' are derived from monocyte/macrophages and secrete angiogenic growth factors," *Circulation*, 107:1164-1169 (Mar. 4, 2003).

Rowley, SD et al. "Isolation of CD34+ cells from blood stem cell components using the Baxter Isolex system," *Bone Marrow Transplant.*, 21:1253-1262 (Jun. 1998).

Stamm, C. et al., "Autologous bone-marrow stem-cell transplantation for myocardial regeneration," *Lancet*, 361:45-46 (Jan. 4, 2003).

Strauer, B. et al., "Repair of infarcted myocardium by autologous intracoronary mononuclear bone marrow cell transplantation in humans," *Circulation*, 106:1913-1918 (Oct. 8, 2002).

Sun, R. et al. "The effects of natural killer-cell depletion on ex vivo expansion of hematopoietic progenitor cells from umbilical cord blood," *Haematologica*, 88:561-569 (May 2003).

Tomita, S. et al., "Improved heart function with myogenesis and angiogenesis after autologous porcine bone marrow stromal cell transplantation," *J. Thorac. Cardiovasc. Surg*, 123:1132-1140 (Jun. 2002).

Tse, HF et al., "Angiogenesis in ischaemic myocardium by intramyocardial autologous bone marrow mononuclear cell implantation," *Lancet*, 361:47-49 (Jan. 4, 2003).

Bosch, M., U.S. Appl. No. 10/517,871, filed Dec. 13, 2004, entitled "Tangential Flow Filtration Devices and Methods for Leukocyte Enrichment."

Grimm et al., "An enhanced and scalable process for the purification of SIV gag-specific MHC tetramer," *Protein Expression and Purification* 23:270-281 (2001).

Nakamura et al., "Enrichment of lineage $^-$CD34$^-$ cells using a newly developed filter system," *British Journal of Haematology* 108:801-804 (2000).

Sekhar et al., "Retroviral transduction of CD34-enriched hematopoietic progenitor cells under serum-free conditions," *Human Gene Therapy* 7:33-38 (1996).

* cited by examiner

TANGENTIAL FLOW FILTRATION DEVICES AND METHODS FOR STEM CELL ENRICHMENT

CROSS-REFERENCES TO RELATED APPLICATIONS

The present application claims benefit to U.S. Provisional Application No. 60/524,511, filed Nov. 24, 2003, the entire disclosure of which is incorporated herein by reference.

BACKGROUND OF THE INVENTION

Cell populations enriched for stem cells are often desired for use in research or therapy. Typical sources of stem cells include bone marrow, whole peripheral blood, leukopheresis or apheresis products, especially from "mobilized" donors, or other less common sources, such as umbilical cord blood and tissue or organ suspensions. Enrichment of stem cells has been done in several ways. Typical methods include density step gradients (e.g., FICOLL-HYPAQUE®, colloidal silica, and the like), elutriation, centrifugation, lysis of erythrocytes by hypotonic shock, and various combinations of these methods. As an example, the purification of stem cells from bone marrow requires removal of erythrocytes and granulocytes, which is often accomplished by FICOLL-HYPAQUE® density gradient centrifugation. There are disadvantages to each of these methods, one of which is the need for laborious washing steps after the enrichment step is performed, e.g., to remove the density gradient centrifugation medium.

Following enrichment, the cells are typically washed by a repetitive process. The steps generally include placing the enriched cell suspension into a centrifuge tube and pelleting the cells to the bottom of the tube by use of a centrifuge. The tube is removed from the centrifuge, and the supernatant is decanted from the pelleted cells. A wash liquid is added to the tube, and the cell pellet is resuspended. These steps are typically repeated 2 to 4 times.

One disadvantage of this washing process is that sequential resuspension and centrifugation can decrease cell viability and increase cell lysis. Another disadvantage of washing by centrifugation is the opportunity for bacteria or other infectious agents to contaminate the cells. Even if all the materials are kept sterile, the repeated opening of the centrifuge tubes, and the exposure of pipettes and bottles of wash solution to the air can result in contamination. The risk of contamination is sufficiently significant that some medical regulatory agencies have demanded that only "closed" systems are used for cell handling.

Filtration methods have also been used to remove cells from blood while retaining other blood constituents for later use. Such methods generally trap the cells on a filter in a non-recoverable form, while allowing other blood constituents to pass through the filter and into a collection vessel. For example, filters are available to remove leukocytes from blood so that the incidence of alloimmune reactions is minimized following blood transfusions. Leukocyte removal is typically done using filters which are made of matted plastic fiber mesh. The mesh is usually arranged to trap the leukocytes in a reticulated matrix having enough depth so that the cells are trapped throughout the depth of the filter, thereby keeping the filter from clogging, as would occur if the leukocytes were trapped on a planar surface.

In addition to the physical trapping of the cells, the materials and large surface area of the filter allow leukocytes to adhere irreversibly to the surface. Many of these adherent cells are the very ones desired for some medical procedures. The resulting combination of trapping and adherence to the filter creates a highly efficient means of removing the leukocytes for disposal prior to blood infusion therapy. However, when leukocytes are the desired cells, this method of filtration is not advantageous.

A method that has been useful in the fractionation of various particles is tangential flow filtration (TFF) or "cross-flow" filtration. TFF relies on the movement of a fluid parallel to the surface of a porous membrane filter. The pores of the membrane allow passage of the fluid and of particles within the fluid that are typically smaller than the pores. In addition, the cross-flow (or "tangential" flow) of fluid parallel to the filter prevents a build-up of particles larger than the pores on the filter surface.

TFF has been used for the gross separation of various materials. The use of tangential flow filtration in the pharmaceutical field has been reviewed by Genovesi (*J. Parenter. Aci. Technol.*, 37:81, 1983), including the filtration of sterile water for injection, clarification of a solvent system, and filtration of enzymes from broths and bacterial cultures. Marinaccio et al. (WO 85/03011) report a process for use in the removal of particulate blood components from blood for plasmapheresis, and Robinson et al. (U.S. Pat. No. 5,423,738) describe the use of TFF for the removal of plasma from blood, allowing the reinfusion of blood cells and platelets into patients.

In another use, TFF has been reported for the filtration of beer (EP 0 208 450), specifically for the removal of particulates such as yeast cells and other suspended solids. Kothe et al. (U.S. Pat. No. 4,644,056) disclose the use of TFF in the purification of immunoglobulins from milk or colostrum, and Castino (U.S. Pat. No. 4,420,398) describes its use in the separation of antiviral substances, such as interferons, from broths containing these substances as well as viral particles and cells. Similarly, TFF has been used in the separation of bacterial enzymes from cell debris. (Quirk et al., *Enzyme Microb. Technol.*, 6:201, 1984). In addition, tangential flow filtration units have been employed in the concentration of cells suspended in culture media. (See, e.g., Radlett, *J. Appl. Chem. Biotechnol.*, 22:495, 1972).

TFF has also been reported to separate liposomes and lipid particles according to size. (Lenk et al., U.S. Pat. No. 5,948,441). TFF allows for the formation and isolation of liposomes and lipid particles having a defined size range from heterogeneous populations of such particles. (See Lenk et al., supra).

However, while TFF has been used for gross fractionation of biological liquids and the separation of, for example, liposomes, the use of TFF for separation of live cell populations differing in defined characteristics has not been appreciated in the art. In particular, the unique problems associated with the selective separation of stem cells from other bone marrow cells or from blood cells and tissue or organ suspensions while maintaining sterility, cell viability and regenerative activity has not been addressed. In addition, the removal of other cell populations such as, e.g., populations with overlapping size ranges, has not been solved by current approaches.

Therefore, there remains a need in the art for additional devices and methods for selectively enriching stem cells from other bone marrow or blood constituents, including plasma, erythrocytes, and/or platelets, while preserving sterility, cell viability and regenerative and cellular activity. The present invention satisfies these and other needs.

BRIEF SUMMARY OF THE INVENTION

The present invention relates to the separation of stem cells or progenitor cells from bone marrow, blood and blood preparations, tissue, and tissue or organ preparations. In particular, a cell population enriched in stem cells is prepared by the use of a tangential flow filtration device. Methods for the use of the device for the preparation of enriched stem cell populations are provided. The cell populations enriched in stem cells and the like obtained by the use of the devices and methods of the present invention can be used to prepare compositions suitable for infusion into individuals for the purpose of for example, bone marrow reconstitution, or for the repair of injured tissue including cardiac muscle, and the like.

A tangential flow filtration device of the present invention comprises a remover unit having a cross-flow chamber, a filtrate chamber and a filter disposed therebetween. The filter is in fluid communication on one side, the retentate surface, with the cross-flow chamber, and on the other side, the filtrate surface, with the filtrate chamber. The cross-flow chamber has an inlet adapted to introduce a sample, such as bone marrow, or blood constituents, comprising stem cells into the cross-flow chamber and parallel to the retentate surface of the filter. An outlet is also provided in the cross-flow chamber centrally disposed in a portion of the chamber opposite the retentate surface of the filter. The filter suitable for use in the tangential flow filtration device typically has an average pore size ranging from about 1 to about 10 microns. In certain embodiments for use in the enrichment of stem cells, the filter has an average pore size of about 3 to about 7 microns, or about 3 to about 5.5 microns. Typically, the remover unit is provided as a single use disposable assembly.

Further, the device can comprise a means for providing a predetermined input rate of the sample into the inlet of the cross-flow chamber and a means for controlling a filtration rate of filtrate through the filter and into the filtrate chamber. The filtration rate controlling means limits the rate of filtration to less than the unopposed filtration rate for the filter. The sample comprising stem cells can be provided by a source device such as a leukopheresis device or a container comprising a sample collected from, for example, a leukopheresis device, and the like.

The tangential flow filtration device can further comprise a recovery unit. The recovery unit comprises an inlet and an outlet that can be interconnected in a loop format with the cross-flow chamber of the remover unit. In this embodiment of the device, the cross-flow chamber inlet is in fluid communication with the recovery unit outlet, and the cross-flow chamber outlet is in fluid communication with the recovery unit inlet. The recovery unit can further comprise a sample inlet and a wash inlet. In certain embodiments of the tangential flow filtration device the sample inlet and wash inlet are a single shared inlet. Typically, the wash inlet is in fluid communication with a source of replacement or wash fluid. The replacement or wash fluid can be, for example, an isotonic buffer or tissue culture media.

The sample inlet of the recovery unit is in fluid communication with a sample source such as bone marrow or blood constituents comprising stem cells. In one embodiment of the present invention the sample source comprising bone marrow or blood constituents is a syringe equipped with a needle, or a specialized device specifically designed for the removal of bone marrow from a donor or a patient. The TFF device and operation of the device is described in greater detail in U.S. Provisional patent application Ser. No. 60/390,730, filed Jun. 19, 2002 and in WO 2004/000444, each incorporated herein by reference in its entirety.

One embodiment of the device of present invention comprises, a tangential flow filtration device for enriching a sample of bone marrow for stem cells. The device comprises a remover unit comprising a cross-flow chamber and a filtrate chamber separated by a filter, wherein the cross-flow chamber has an inlet and an outlet, the outlet centrally disposed in an upper portion of the chamber, and wherein the inlet is disposed above the filter and introduces fluid into the cross-flow chamber substantially parallel to the filter; a means for providing a predetermined input rate of the sample through the cross-flow chamber inlet; and a means for modulating a filtration rate through the filter; wherein the filter has a pore size of about 5 microns; and whereby the sample is enriched for stem cells in a retentate in the cross-flow chamber.

In another embodiment of the present invention, a tangential flow filtration device for enriching a sample of blood constituents for stem cells is provided wherein the device comprises a remover unit, wherein the remover unit comprises a cross-flow chamber below a filtrate chamber and separated by a filter, the cross-flow chamber having an inlet and an outlet, the outlet centrally disposed in a lower portion of the chamber, and wherein the inlet is disposed below the filter and introduces fluid into the cross-flow chamber substantially parallel to the filter; a means for providing a predetermined input rate of the sample through the cross-flow chamber inlet; and a means for maintaining a filtration rate through the filter; wherein the filter has a pore size of about 5 microns; and whereby the sample is enriched for stem cells in a retentate in the cross-flow chamber.

The present invention also provides methods for separating stem cells from a sample of bone marrow constituents, blood constituents, tissue, or tissue or organ preparations comprising stem cells. The method steps comprise: (1) introducing the sample into a remover unit through an inlet in the remover unit; (2) subjecting the sample to cross-flow substantially parallel to a filter having a pore size of about 1 to about 10 microns; (3) subjecting the fluid to filtration through the filter; and (4) selectively removing non-stem cell constituents from the sample to form a cell population enriched for stem cells. The sample can be subjected to a partial purification or enrichment by leukopheresis, density centrifugation, differential lysis, filtration, or preparation of a buffy coat, prior to introduction into the remover unit. In one embodiment, the sample is induced to flow across the filter surface with a vortex motion in the cross-flow chamber. Additionally, the cell population enriched for stem cells can be washed with a wash solution.

In one particular embodiment of the present invention a cell sample, such as a sample of bone marrow constituents comprising stem cells, is contacted with a pretreatment solution comprising an agent that causes shrinkage of cells in the sample that are of a nominal size similar to the stem cells. The shrunken cells are susceptible to passing through the filtration membrane providing a cell population more enriched for stem cells. In one specific embodiment the cells induced to undergo shrinkage are granulocytes, such as neutrophils and the like. One particular solution useful in this embodiment comprises, for example, an effective amount of dimethyl sulfoxide (DMSO) in a physiologically acceptable solution. The physiologically acceptable solution can be, for example, a hypotonic salt solution such as diluted phosphate buffered saline (PBS). Alternatively, the pretreatment solution can comprise a hypertonic solution containing, for example, a sugar such as mannitol or glucose, or can be a hypertonic salt solution. In yet another embodiment, the cells in which shrinkage is induced are prevented from re-swelling by treating or pretreating the cell sample with an agent that prevents swelling of the shrunken cells. In one embodiment the anti-swelling agent is an agent that prevents tyrosine phosphorylation, such as for example, genistein and the like. In still another embodiment the anti-swelling agent inhibits the action of the sodium-hydrogen exchanger. In yet another embodiment the solution in which the cell sample, e.g., comprising bone marrow constituents, is suspended is free of sodium salts which blocks the exchange of hydrogen and sodium by the sodium-hydrogen exchanger preventing induction of re-swelling of the cells.

In the methods of the present invention the non-stem cell constituents removed from the cell sample include for example stroma, plasma, platelets, erythrocytes, and the like. The enriched cell population can comprise at least about 10% stem cells, but typically comprises at least about 20%, or more, stem cells. In one embodiment of the method of the present invention steps (1), (2), and (3) are repeated at least two times to form the cell population enriched for stem cells. The cell population enriched for stem cells can be used for infusion into patients in need of stem cell therapy.

In additional embodiments, the cell population enriched for stem cells can be induced to form other cell types useful in therapy including, for example, endothelial cells, smooth muscle cells, heart muscle cells, neurons, dendritic cells, and other cell types. Various stem cell induction methods are well known to the skilled artisan.

Cell samples used in the methods of the present invention are typically collected from an individual donor. The donor can be the patient to receive stem cell therapy or another individual. Prior to collection of the cell sample from a donor, the donor can have undergone treatment with a stem cell mobilizing agent, such as for example, M-CSF, G-CSF, GM-CSF, or high- or low-dose cyclophosphamide, and the like to produce a cell population enriched for hematopoietic stem cells. The stem cell mobilizing agent induces the proliferation of $CD34^+$ stem cells which are released into the peripheral blood stream. Bone marrow, blood, e.g., a leukapheresis sample, tissue, or tissue or organ preparation from the individual donor is then introduced into a tangential flow filtration (TFF) unit of the present invention. The TFF unit comprises a cross-flow chamber, a filtrate chamber, and a filter in fluid communication with the cross-flow chamber and the filtrate chamber. Typically, the filter used in the TFF device has a pore size of about 3 to about 5.5 microns. The cell sample enriched for hematopoietic cells is recirculated through the TFF unit at a predetermined input rate and a predetermined filtration rate, the predetermined input rate is typically at least five times the predetermined filtration rate; and the predetermined filtration rate is less than the unopposed filtration rate for the filter; providing an isolated cell population enriched for $CD34^+$ leukocytes. The method can result in an enriched cell population that is substantially free of non-leukocyte blood constituents including plasma, platelets and erythrocytes. The enriched cell population produced by this method can increase the percentage of $CD34^+$ cells to comprise about 2% to about 10%, to about 5% to about 40%, or more of the cell population.

A further understanding of the nature and advantages of the invention will become apparent by reference to the remaining portions of the specification.

BRIEF DESCRIPTION OF THE DRAWINGS

FIG. 1A provides an embodiment of the device for the enrichment of leukocytes wherein the cross-flow chamber is above the filtration chamber. FIG. 1B depicts a front view of the device wherein the input of sample is below the filter and the filtrate passing upward through the filter for the enrichment of monocytes. FIG. 1C is an overhead view of the device depicted in FIG. 1B.

DESCRIPTION OF THE SPECIFIC EMBODIMENTS

Figure 1A:
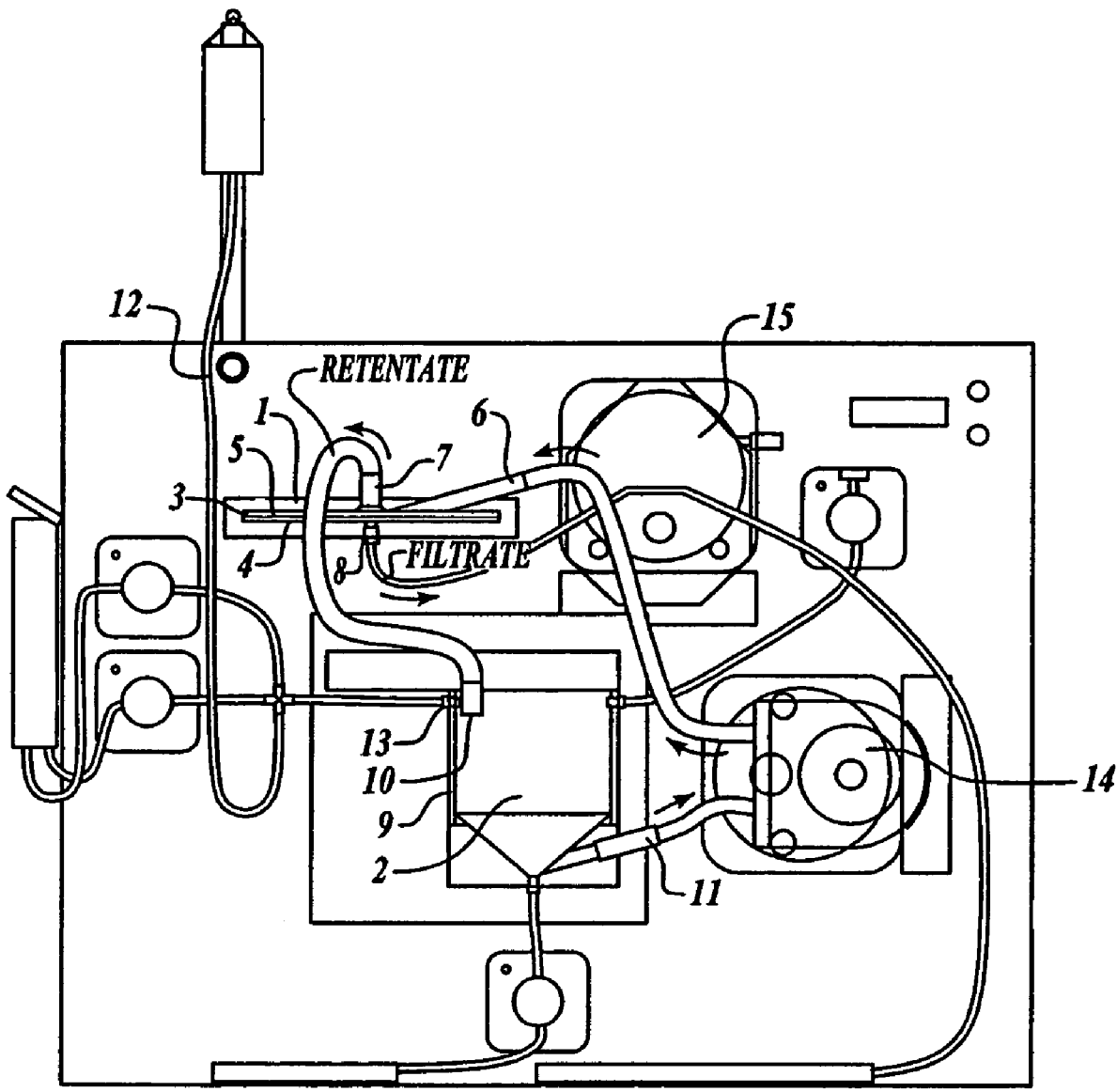
FIGS. 1A through 1C depict embodiments of the tangential flow filtration device for the separation of leukocytes and also monocytes from a blood product sample.

The present invention provides methods for processing a cell sample comprising a heterogeneous mixture of bone marrow constituents, blood constituents, tissue, or tissue or organ suspensions to provide an enriched population of stem cells. In one aspect of the invention, methods are provided for the enrichment of stem cells by the selective removal of non-stem cells constituents, e.g., stroma, plasma, platelets and/or erythrocytes, and the like. In another aspect, methods are provided for the enrichment of stem cells by the selective removal of other large cell types, including polymorphonuclear cells, such as for example, granulocytes, from the mixture. In a particular method a bone marrow sample can be treated with an agent that shrinks non-stem cells of approximately the same size such that the shrunken non-stem cells pass through a filter of a TFF device and are separated from the stem cells.

An enriched population of stem cells is typically prepared from a sample, or fluid mixture, comprising bone marrow constituents. The term "bone marrow constituents" as used herein refers to any material typically present in bone marrow, including such material typically present in diseased as well as non-diseased states. Bone marrow constituents include stem cells and can include, for example, lymphocytes, monocytes, erythrocytes, neutrophils, eosinophils, natural-killer (NK) cells, and/or platelets, soluble or insoluble protein or protein complexes (e.g., enzymes, immunoglobulins, or immunoglobulin-antigen complexes), other macromolecular components such as, e.g., lipids, or any other portion of whole blood that can be physically separated, irrespective of its precise molecular or cellular makeup, including, e.g., stroma, plasma or serum.

The sample, or fluid mixture, can be partially enriched for stem cells prior to carrying out the methods of the present invention. The term "stem cell" is used interchangeably with the term "precursor cells" "progenitor cells" or "$CD34^+$ cells". These terms include hematopoietic stem cells, which include, e.g., lymphoid, myeloid and erythroid progenitor cells, as well as progenitor cells that can give rise to endothelial cells; muscle cells, including smooth muscle cells and heart muscle cells; neuronal cells and skeletal cells, including those that form bone and cartilage.

In certain aspects of the present invention, a cell population containing polymorphonuclear cells (PMNs) or granulocytes are separated from the stem cells. This population typically contains neutrophils, eosiniphils and basophils and their precursors, and is referred to as PMNs in this application.

As used herein, the term "population of stem cells" refers to any group of cells that includes stem cells. A population of stem cells can include, as above, a broad range of stem cell sub-types or of particular sub-types, such as, e.g., endothelial cell or muscle cell precursor or progenitor cells. The terms "enrichment", "enrich" and "enriched" mean that the processing of a mixture of bone marrow constituents using a device as briefly described herein and more fully described in U.S. Provisional patent application Ser. No. 60/390,730, filed Jun. 19, 2002 and in WO 2004/000444, (each incorporated herein by reference in their entirety), and following the methods of the present invention results in a cell population having a higher percentage of viable stem cells, in relation to other constituents, than the initial cell sample (i.e., prior to enrichment). As used herein, the term "viable" refers to a stem cell that is capable of differentiation under suitable culture conditions or upon reinfusion into a patient or a suitable animal model.

The devices according to the present invention utilize tangential flow filtration to enrich for a population of stem cells. The terms "tangential flow filtration" and "cross-flow filtration" are used interchangeably and refer to the separation of suspended particles (e.g., cells) from a fluid mixture, including the separation of particles of a defined characteristic (e.g., a desired size range) from a heterogeneous mixture of particles in the fluid mixture. The particles are separated by passing or circulating the fluid mixture (e.g., a sample fluid) in a sample chamber substantially parallel or tangential to a filter (e.g., the surface of the filter facing the sample fluid), typically under some positive pressure, with the fluid mixture comprising the concentrated particles, or stem cells, continuing to flow tangential to the membrane surface.

Generally, determination of which particles are removed in the "filtrate," i.e., that portion of fluid passing through the filter, and those particles retained in the "retentate" is dependent on a variety of factors. Such factors include, e.g., filter pore size, input rate, filtration rate, concentration of particles in the fluid mixture, temperature, and viscosity of the fluid mixture. As used herein, "pore size" refers to the average size of the pores in the filter. "Input rate" refers to the rate at which a sample (e.g., a fluid mixture) is introduced into the chamber housing the filter. Where the sample is recirculated multiple times across a filter (e.g., in one particular embodiment of the device according to the present invention), the input rate is also referred to as the "recirculation rate." "Cross-flow" refers to the substantially parallel (i.e., parallel to the surface of the filter in any direction) flow of the fluid mixture across the filter. "Cross-flow rate" refers to the rate of flow of sample, or fluid mixture, over and substantially parallel to the filter. The cross-flow rate of the fluid mixture is generally dependent on a variety of parameters, including, for example, the input rate and the size and shape of the chamber housing the filter. "Filtration rate" refers to the rate of flow of the fluid mixture through the filter. The filtration rate for a device and the methods according to the present invention is typically less than the unopposed (i.e., open tube) filtration rate. "Output rate" refers to the rate of removal of the fluid mixture from the cross-flow chamber, other than the fluid mixture passing through the filter (i.e., the filtrate). The output rate is generally equal to the input rate minus the filtration rate.

As used herein, the term "filter" refers to any article made of any material or combination of materials having a plurality of pores that allow one or more components (e.g., blood and/or bone marrow constituents) of a sample or fluid mixture subjected to cross-flow across the article to pass through it, thereby separating those components (e.g., non-stem cells, proteins, plasma, serum, platelets, and the like) from other components (e.g., stem cells). The surface of a filter can have any suitable area, such as, for example, about 42 to about 145 mm in diameter, although filters of greater and lesser area can be used. In certain embodiments, only one filter is used in a TFF device. In other embodiments, additional filters can be used in a TFF device.

The filter typically employed in the TFF device of the present invention can be chosen from a wide range of organic polymeric filters. Such filters include, but are not limited to, microporous membranes of nylon, polyvinylidene fluoride (PVDF), cellulose acetate/nitrate, polysulfone, polycarbonate, polyethylene, polyester, polypropylene, and polyamide. Other filters, such as ceramic filters and metallic filters, can also be used. Both hydrophilic and hydrophobic, charged and uncharged filters can be used. In certain applications, hydrophilic filters can be preferred.

A filter of the present invention typically comprises a number of pores distributed across the area of the filter. In certain embodiments, the filter has a plurality of pores with a small variation in pore size. For example, the variability in the pore size can be about ±20%, or within the range of about ±0% to about ±20%. In a typical embodiment, "nuclepore" or "track etched" filters are used (e.g., Poretics® polyethylene or polycarbonate track-etched filter membranes (Osmonics, Minnetonka, Minn.)). These filters typically have a smooth surface with tightly controlled pore sizes in the material. Such filters are typically prepared by exposing a flat sheet of nonporous plastic to a source of radioactive particles, which are energetic enough to pierce the plastic sheet. The "tracks" are then enlarged in diameter by exposure to chemical solvents or etching agents. The size of the pores can be controlled by the track etching conditions.

The present invention takes advantage of differences between various cell types in bone marrow, blood, tissue, or tissue or organ suspensions to enrich for stem cells. Such differences can include, e.g., differences in size, shape and/or deformability. The size and deformability of cells in human bone marrow, blood, tissue, or tissue or organ suspensions typically varies by cell type. Erythrocytes (red blood cells) typically are biconcave disk shaped, enucleate, measure about 7 microns in the major diameter and are relatively deformable. Polymorphonuclear leukocytes cells are typically spheroidal, also about 7 microns, but less deformable than erythrocytes. Of the mononuclear cells, lymphocytes are typically 7 to 10 microns, and monocytes usually are in the range of 10 to 15 microns. Stem cells are generally in the same size range as monocytes.

In various embodiments, the filter pore size is selected to enrich for stem cells, and/or to fractionate bone marrow, blood constituents, tissue, or tissue or organ suspensions, thereby enriching the collected cell population for stem cells. For example, in certain embodiments, stem cells having a nominal diameter of 10 to 15 microns, and erythrocytes having a nominal diameter of 7 microns, can be separated by TFF using a filter having a pore size of about 5 microns.

In other embodiments, the filter pore size can be within the range of about 1 to about 10 microns, about 3 to about 8 microns, or about 3 to about 5.5 microns. A filter pore size in the range of about 3 microns can retain most stem cells and leukocytes, and effect less efficient removal of erythrocytes from the stem cells. In contrast, a filter pore size in the range of about 8 microns can effect more efficient removal of erythrocytes, but increases the loss of stem cells and leukocytes in the filtrate. A filter size of about 3 to about 5.5 microns is typically used to enrich for stem cells.

The enrichment of stem cells from other bone marrow, blood, tissue, or tissue or organ suspension constituents can also be affected by the input rate, the filtration rate, and/or the concentration of cells in the sample or fluid mixture. For example, erythrocytes are more deformable than other cell types and can, therefore, be more readily passed through a filter with a pore size smaller than the major diameter of the erythrocytes (e.g., less than about 7 microns). In a specific example, erythrocytes can be separated from leukocytes using filters having pore size of about 5.5 microns.

The enrichment of stem cells from other cellular bone marrow constituents, or tissue or organ suspension constituents can also be effected by maintaining a filtration rate that is less than the unopposed (i.e., open tube) filtration rate under the same input or recirculation rate. In other embodiments, the loss of leukocytes to the filtrate can be reduced by maintaining an input or recirculation rate that is greater than the filtration rate. In exemplary embodiments, the input or recirculation rate can be at least about five times, at least about 10 times, at least about 20 times, at least about 50 times, or at least about 100 times, the filtration rate.

A sample, or fluid mixture, comprising various bone marrow constituents, blood constituents, tissue, or tissue or organ suspensions for stem cell fractionation by TFF can be obtained from a variety of sources and can include fluid mixtures of blood products at any of the various stages of processing. For example, bone marrow and blood sources can be either human or non-human. In addition, fluid mixtures can be, for example, bone marrow, whole blood, various dilutions of whole blood, or whole blood or blood dilution that has been subjected to processing by, e.g., removal of plasma or other blood constituents, or tissue or organ suspensions. Thus, the fluid mixture can include, for example, a blood cell population that is already at least partially enriched for stem cells.

Bone marrow or blood constituents, populations of bone marrow or blood cells, or suspensions of tissue or organs, can be prepared by methods known to those skilled in the art. Such methods typically include collecting heparinized bone marrow or blood, apheresis or leukopheresis, preparation of buffy coats, rosetting, centrifugation, density gradient centrifugation (e.g., density gradient materials including, FICOLL-HYPAQUE®, PERCOLL®, sucrose, and the like), differential lysis of non-leukocyte cells, filtration, and the like.

The fluid mixture comprising the bone marrow or blood constituents can optionally be diluted or concentrated, as desired. For example, in certain embodiments, the bone marrow or blood constituents are diluted 1:2, 1:5, 1:10, or any other suitable dilution. Bone marrow or blood constituents can be diluted in, for example, isotonic buffers (e.g., PBS or HEPES-buffered saline), tissue culture media and the like. Typically, the sample of bone marrow or blood constituents subjected to TFF has a cell concentration of about $10^6$ to about $10^8$ cells per ml of which at least about 10 to 20% are stem cells. In addition, the number of PMNs is reduced from about 60 to about 75% of the cell number to about 50% or less.

Bone marrow or blood cell populations, or tissue or organ suspensions, can be obtained from a variety of types of subjects, according to the desired use of the enriched population of stem cells. The subject, for example, can be a healthy subject. Alternatively, cells can be obtained from a subject in need of bone marrow reconstitution, such as, for example, a cancer patient who has been found to have damaged bone marrow due to chemotherapeutic treatments. A bone marrow or blood cell population can also be collected from an individual that has been administered a stem cell mobilization agent such as for example M-CSF, GM-CSF, G-CSF, or low- or high-dose cyclophosphamide (Deliliers et al., *Leuk. Lymphoma* 43:1957, 2002) and the like. The individual can be a patient that will receive the enriched cell population, a relative, or an HLA-matched individual.

Figure 1B:
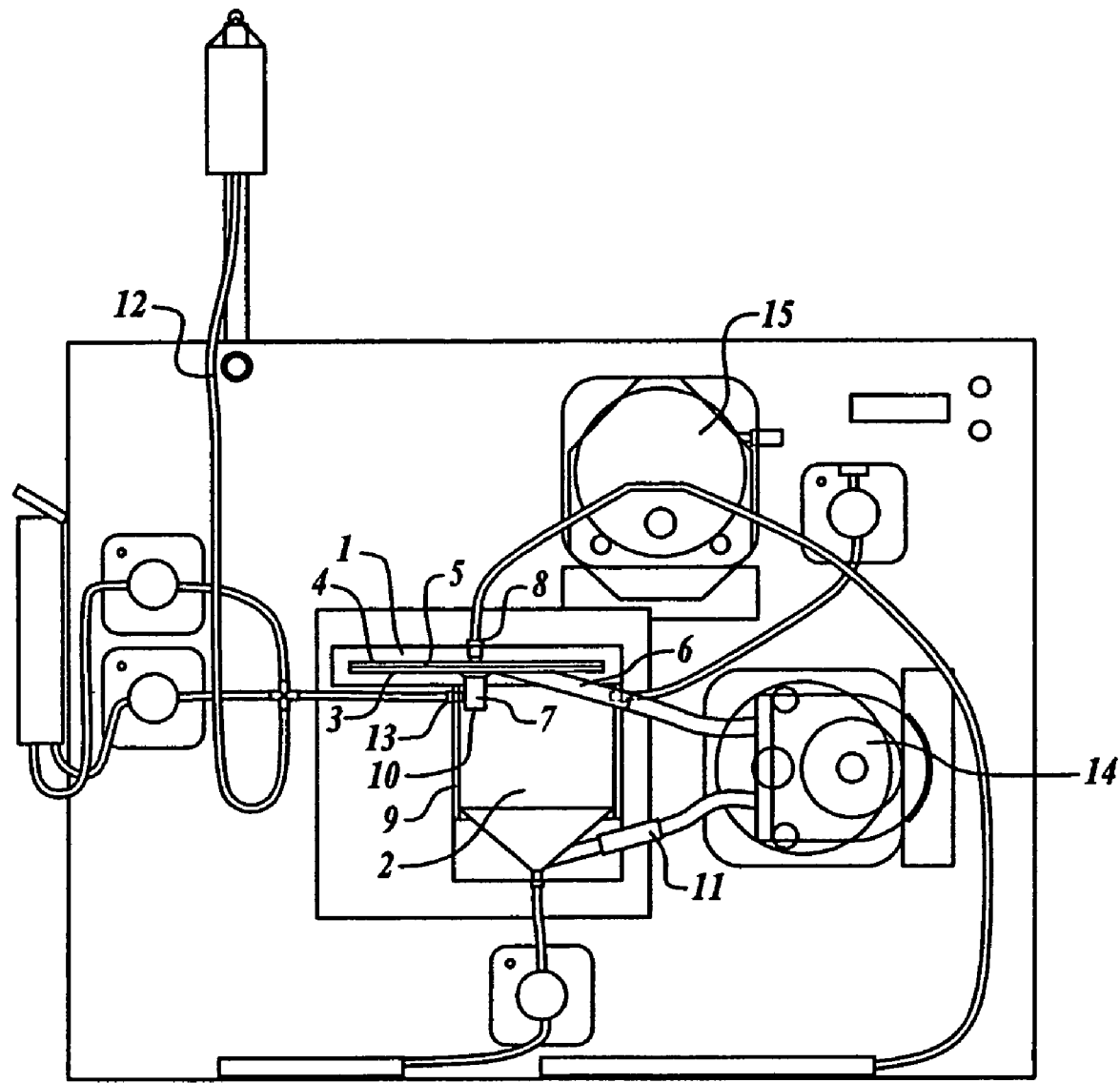
Figure 1C:
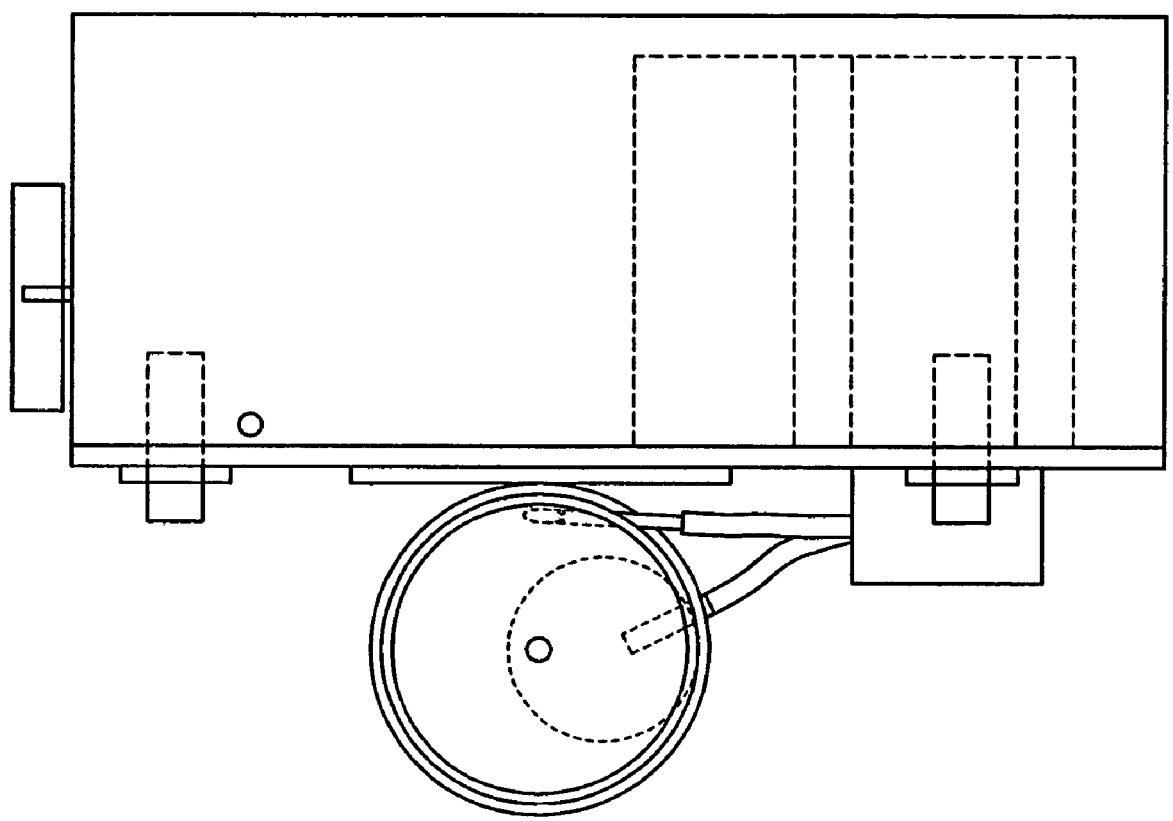

The devices according to the present invention as depicted in FIGS. 1A through 1C typically comprise a cross-flow chamber (3) and a filtrate chamber (4). A filter (5) is positioned between and with one surface in fluid communication with the cross-flow chamber (the retentate surface) and other surface in fluid communication with the filtrate chamber (the filtrate surface). The cross-flow chamber, filtrate chamber and filter comprise a remover unit (1). The remover unit can be provided as a single use disposable assembly, sterilized and prepared for use in an isolation method of the present invention. A remover unit assembly would be used for each sample to be enriched for stem cells. In one particular embodiment of the present invention, the cross-flow chamber typically has a volume of about 55 ml, and the filtrate chamber has a volume of about 25 ml. The filter diameter is typically substantially the same as the diameter of the cross-flow chamber. In certain embodiments used to demonstrate the utility of the present invention, the filter is about 140 mm to about 143 mm in diameter.

In the methods of the present invention the fluid mixture enters the cross-flow chamber (3) through a fluid inlet (6) that is typically situated adjacent to the retentate surface of the filter and such that the fluid mixture (e.g., sample) enters the chamber substantially parallel to the retentate surface of the filter. Typically, fluid is removed from the cross-flow chamber (3) through a fluid outlet (7), which is usually located at a portion of the cross-flow chamber perpendicular to the retentate surface of the filter. In certain exemplary embodiments, the cross-flow chamber inlet (6) diameter is about 7 mm to about 8 mm, and cross-flow chamber outlet (7) diameter is about 8 mm to about 10 mm. The filtrate is removed through an outlet (8) in the filtrate chamber (4).

Typically, the fluid mixture is introduced into the cross-flow chamber at a sufficient input rate such that the cross-flow of the fluid mixture across the surface of the filter (retentate surface) is at a velocity high enough to gently disrupt and back-mix fluid and cells at the contact surface of the filter, i.e., the boundary layer. As used herein, "boundary layer" refers to that layer of fluid adjacent to and on the retentate side of the filter, typically left by fluid passing through the filter. This disruption of the boundary layer facilitates efficient filtration by preventing the material at the contact surface of the filter from binding to the filter or becoming stagnant, which can hinder efficient filtration. The input rate of the fluid mixture is usually not sufficient, however, to cause lysis of a substantial number of leukocytes.

In certain embodiments, the bone marrow or blood constituents are passed across the retentate surface of the filter by pumping the fluid mixture into the cross-flow chamber (3). The pump used to drive the cross-flow of fluid across the filter is referred to as the "cross-flow pump" or "recirculating pump" (14). The cross-flow pump can include any pumping device in fluid communication with the cross-flow chamber (3) sufficient to introduce the fluid mixture into the chamber and across the filter at the specified input rate, without causing substantial damage to the cells (e.g., cell lysis). A cross-flow pump suitable for use in the present invention can include, e.g., a peristaltic pump, piston pump, diaphragm pump, or roller pump. A peristaltic pump can be used, for example, where it is desired to maintain the TFF device as part of a "closed" system.

The fluid mixture is typically pumped into the cross-flow chamber (3) at an input rate that exceeds the filtration rate. In an exemplary embodiment, the input rate is about 1680 ml/minute, and the filtration rate is about 15 ml/minute. In other exemplary embodiments, the input rate is about 1600 to about 1800 ml/minute, and the filtration rate is about 10 to about 20 ml/minute. Non-stem cell material (e.g., erythrocytes, immune complexes, proteins, PMNs, and the like) pass through the filter (5) into a filtrate chamber (4).

As discussed supra, the filtration rate is typically less than the unopposed (i.e., open tube) rate. The filtration rate can be controlled, for example, by reducing or restricting the size of the filtrate chamber outlet, by use of a second pump means (e.g., a "filtration pump") to restrict the flow, and the like.

In another exemplary embodiment, the introduction of a fluid mixture into the device creates a vortex motion within the fluid. This can be done, for example, by introducing the fluid mixture, substantially parallel to a circular filter in a cylindrical cross-flow chamber, at for example an input rate about 5 or about 10 to about 100 times the filtration rate. The flow through is removed by means of an outlet (7) located in the cylindrical chamber perpendicular to the filter and typically adjacent to the center of the filter surface. This arrangement causes the flow to spiral inward toward the center of the filter. The flow is typically not turbulent, or at such a high rate, so as to cause substantial lysis of the stem cells. As discussed above, the cross-flow can also "scrub" the filter surface to prevent binding or stagnation at the boundary layer. By calibrating the input rate such that it is large (e.g., at least about 5 times) relative to the filtration rate, the resulting enriched population of stem cells can be at least about 5, or at least about 20, or at least about 60 percent, or more, stem cells when compared to the percentage of stem cell to the total cell number in the sample cell population.

In another exemplary embodiment, the retentate is recirculated to increase the efficiency of separation. For example, a fluid mixture comprising bone marrow or blood constituents, or a tissue or organ preparation can be introduced into the cross-flow chamber, and during the filtration retentate can be withdrawn through the fluid outlet (7) in the cross-flow chamber to another chamber, such as, e.g., a chamber from which the fluid was initially provided ("a recovery unit"; (2)). The fluid mixture in the recovery unit can then be re-introduced into the cross-flow unit. By connecting the recovery unit (2) and remover unit (1) in a "loop format," continuous recirculation and filtration of the fluid mixture can be achieved. Alternatively, the retentate can be withdrawn through the fluid outlet (7) of the cross-flow chamber (3) and directly reintroduced into the cross-chamber inlet (i.e., without passing through a recovery unit or another chamber). The fluid mixture can be passed through the cross-flow unit for any suitable period of time. In certain embodiments, the fluid mixture can be re-circulated for about 5 to about 60 minutes, or more, to achieve the desired stem cell purity or enrichment.

In yet another embodiment, the volume of the fluid mixture can be adjusted by adding a buffer, a wash solution or other solution (collectively referred to as a "replacement liquid"). The wash solution can, for example, be combined with a fluid mixture in the recovery unit (e.g., through a solution inlet; (13)), in the remover unit, at a pump (14), in tubing extending to or from the remover unit, or at any other convenient location. The cells in the retentate can thus be enriched and washed in the same operation. Typically, the wash solution is isotonic with the cells. Suitable buffer and wash solutions can include a variety of buffers (e.g., phosphate-buffered saline (PBS) or HEPES-buffered saline), tissue culture media, and the like.

In certain embodiments, a cell sample comprising a cell population from, for example, bone marrow, blood, tissue, or a tissue or organ preparation, is enriched for a population of stem cells in a closed, aseptic system. As used herein, the term "closed, aseptic system" or "closed system" refers to a system in which exposure to non-sterile, ambient, or circulating air or other non-sterile conditions is minimized or eliminated. Closed systems for enriching cell populations generally exclude centrifugation in open top tubes, open air transfer of cells, culture of cells in tissue culture plates or unsealed flasks, and the like. The entire filtration system, including, e.g., any cell containers, incubators, tissue culture vessels, or other apparatus for cell processing (infra), can be maintained as a "closed" system. In a typical embodiment, the closed system allows aseptic enrichment of stem cells and, optionally, transfer from an initial collection vessel to a sealable tissue culture vessel, without exposure to non-sterile air. Typically, a peristaltic pump (FIGS. 1A and 1C; (15)) means is used in a closed system.

In another aspect of the invention, a heterogeneous mixture of bone marrow or blood constituents, or tissue or organ suspension is substantially enriched for stem cells by the selective removal from the mixture of non-stem cell bone marrow or blood constituents, including, e.g., stroma, plasma, platelets, erythrocytes, and the like. As used herein, the term "substantially enriched" means that the cell population recovered in the retentate, following as many cycles of recirculation as desired, is comprised typically of at least about 5%, more typically at least about 20%, or at least about 60%, of the desired cell type (e.g., stem cells). In other embodiments, a heterogeneous mixture of bone marrow or blood constituents, and the like, is enriched for stem cells to form an enriched population of stem cells that is substantially free of non-stem cell constituents. As used herein, the term "substantially free" means that the enriched population of stem cells comprises at least about 10% to about 50% stem cells.

It has been determined that certain variables affect the performance of the device. For example, pore size of the filter, total volume of liquid, the recirculation and filtration rates, as well as the ratio between these two rates and the run time can affect the yield of stem cells. To determine optional separation conditions for stem cells, separation runs can be performed using variations in the parameters wherein the cell concentrate (retentate) and the filtrate are sampled at timed intervals to monitor the performance over time. From these results the optional filter pore size, total system volume, recirculation and filtration rates can be determined.

In an exemplary embodiment of this aspect of the present invention, the TFF device comprises a cross-flow chamber (3) with a volume of about 55 ml and a filtrate chamber (4) with a volume of about 25 ml. Further the device comprised the following: a filter having a plurality of pores with a pore size of about 1 to about 10 microns, more typically about 2 to about 8 microns, or even more typically about 3 to about 5 microns; a filter diameter of about 142 mm. In this embodiment the input rate is set to be about 1600 to about 1800 ml/min; and the filtration rate is about 12 to about 17 ml/min. The initial fluid mixture typically has a cell concentration of at least about $10^7$ cells per ml (e.g., leukocytes and other cells). The enriched stem cell population achieved with this embodiment of the invention comprises about 11 to about 20 million cells stem cells representing from about 10% to about 20% of the total number of cells.

In another aspect of the invention, a heterogeneous mixture of bone marrow or blood constituents is substantially enriched for stem cells by the selective removal of non-stem cell constituents, including, for example, the removal of stroma and lymphocytes from the mixture. As used herein, the terms "selective removal", "selectively removed" and "selectively removing" refer to the preferential removal of one cell type and enriching for another cell type. In an exemplary embodiment of this aspect, the TFF device comprises a cross-flow chamber (3) with a volume of about 55 ml and a filtrate chamber (4) with a volume of about 25 ml. Further, the device comprised the following: a filter pore size of about 1 to about 10 microns, or about 2 to about 8 microns, or about 3 to about 5 microns; an input rate of about 1600 to about 1800 ml/min; a filtration rate of about 12 to about 17 ml/min; and a filter diameter of about 142 mm. The initial fluid mixture typically has a cell concentration of at least about $10^7$ cells per ml (e.g., stem cells and other cells). In this embodiment the device was operated in an inverted manner.

In yet another embodiment of the present invention, a heterogeneous mixture of blood constituents from bone marrow, blood, tissue, or from a tissue or organ preparation is pre-treated to facilitate removal of certain cell types that have similar size and deformability as stem cells. Such cells can include polymorphonuclear granulocytes, including neutrophils, eosiniphils, basophils, and the like. In one embodiment this pretreatment comprises the contacting of the bone marrow or blood constituents with an agent that can effectuate an osmotic gradient across the cell membrane, thereby inducing cell shrinkage through the efflux of water. Such agents can include, and are not limited to, dimethylsulfoxide, glycerol, sodium chloride and the like. When DMSO is used, the final effective DMSO concentration can be between about 5% and about 20%, or between about 10% and about 15%. In a particular embodiment, the effective DMSO concentration is about 12.5% or about 15%. DMSO can be dissolved in a buffer or physiologically acceptable solution with low ionic strength. Another agent that can be used is glycerol. The effective amount of glycerol is between 0.5 mol/L and about 2.5 mol/L. In a specific embodiment the final glycerol concentration is about 1 mol/L. Contacting the cells with these agents can lead to lysis of the unwanted granulocytes. Lysis can be effected through sequential exposure to DMSO and glycerol. The solution used can comprise a solution medium with low osmotic strength. The induced shrinkage of the undesired cells makes these cells more amenable to removal through filtration and allow selective removal of these cell populations by tangential flow filtration. Effective amounts of an agent that prevents the re-swelling of the cells during the separation process can also be included. Such agents can include, but are not limited to, an agent that prevents tyrosine phosphorylation such as genistein, or an agent that inhibits the action of the sodium-hydrogen exchanger.

Culture, Expansion and Differentiation of Enriched Cell Populations

In one embodiment of the present invention, the methods of the present invention are used to obtain an enriched population of stem cells which can be used to produce a composition useful in, e.g., allogeneic or autologous transplantation. In particular embodiments, the enriched population of stem cells is further enriched for hematopoietic stem cells following the tangential flow separation procedure. Methods for enrichment of hematopoietic stem cells from a source of peripheral blood leukocytes are known in the art and can be adapted for use with an enriched population of stem cells isolated as described herein. For example, an enriched population of stem cells can be further enriched for CD34$^+$ cells using, e.g., immunomagnetic separation techniques (see, e.g., Rowley et al., *Bone Marrow Transplant.* 21:1253, 1998; Denning-Kendall et al., *Br. J. Haematol.* 105:780, 1999). The bone marrow or blood donor can be isolated from the patient to receive the transplant, a close relative, a HLA-matched individual, or the like.

In yet another embodiment, the methods of the present invention are also used to obtain a non-stem cell subset such as, for example, a cell population enriched in progenitor cells (e.g., hematopoietic or endothelial progenitor cells) or cells that secrete a factor of interest (e.g., hematopoietic or angiogenic growth factors). For example, circulating endothelial progenitor cells (CEPs) can be identified as a subset of circulating CD34$^+$ cells by, e.g., coexpression of VEGFR-2 and AC133 (as well as, e.g., VE-cadherin and E-selectin). (See, e.g., Peichev et al., *Blood* 95:952, 2000.) An enriched population of leukocytes can be further enriched for CEPs using, for example, immunomagnetic separation techniques with antibodies directed to VEGFR-2 and AC133. Also, CEPs can be mobilized in an individual donor prior isolation of a cell population from the donor and enrichment using TFF. In this method the donor can be treatment with a cytokine such as, e.g., VEGF. (See, e.g., Gill et al., *Circ Res.*, 88:167, 2001). Further, in yet other embodiments, endothelial-like circulating angiogenic cells (CACs) (which secrete, e.g., VEGF, HGF, G-CSF, and GM-CSF) are obtained by culturing an enriched population of leukocytes with, e.g., VEGF, bFGF, IGF-1, EGF, and FBS on a fibronectin-coated surface and then discarding non-adherent cells (see, e.g., Rehman et al., *Circulation* 107:1164, 2003).

In addition, the enriched population of stem cells can be cultured to induce expansion of pluripotent progenitor or stem cells. For example, CD34$^+$ stem cells can be expanded in vitro by culture with hematopoietic growth factors such as, e.g., a combination IL-1, IL-3, IL-6, stem cell factor (SCF), granulocyte-monocyte colony-stimulating factor (GM-CSF) and G-CSF (see, e.g., Sun et al., *Haematologica* 88:561, 2003). The progenitor or stem cells can subsequently be treated with any of various cytokines and growth factors to induce differentiation into cells of hematopoietic or non-hematopoietic lineages.

In other embodiments, an enriched population of stem cells can be cultured under conditions suitable for inducing differentiation (e.g., differentiation of progenitor cells or transdifferentiation of more differentiated cells types such as, for example, monocytes or monocyte-derived dendritic cells). (As used herein, "transdifferentiation" refers to a process of phenotypic modulation of a differentiated cell, generally without the need for any cell division, whereby the differentiated cell differentiates into a morphologically and/or functionally different cell type.) For example, in addition to differentiation into dendritic cells, monocytes can be transformed into other hematopoietic or non-hematopoietic cell types, including, e.g., macrophages, osteoclasts, and endothelial-like cells, depending on culture conditions (see, e.g., Becker et al., *J. Immunol.* 139:3703, 1987; Nicholson et al., *Clin Sci.* 99:133, 2000; Havemann et al., in *Novel Angiogenic Mechanisms: Role of Circulating Progenitor Endothelial Cells* 47-57 (Nicanor I. Moldovan eds., 2003)). Also, an enriched population of leukocytes can be cultured under conditions that induce differentiation of relatively undifferentiated cell subsets (e.g., pluripotent progenitor and stem cells) into hematopoietic or non-hematopoietic lineages using any of various cytokines or growth factors. Such differentiation can be induced prior to or following cell expansion by methods known to the skilled artisan.

In certain embodiments of this invention the population of cells enriched for stem cells can be used to affect the regeneration or repopulation of cells or tissues in a person in need of such regeneration or repopulation. Such a person can be suffering from any condition where the patient would benefit from the administration of stem cells, including Parkinson's Disease, diabetes, chronic heart disease, kidney disease, liver failure, cancer, spinal cord injury, multiple sclerosis, Alzheimer's Disease, or could be in need of gene therapy to prevent a genetic or epigenetic defect In certain embodiments of the present invention, the recipient of the stem cells is autologous or can be allogeneic to the donor. The recipient can be in need of bone marrow regeneration because the individual has undergone myeloablative therapy. In another example, the recipient can be in need of repair of cardiac tissue because the individual has undergone a cardiac infarct or is suffering from congestive heart failure or cardiac insufficiency. In either case the enriched stem cell population isolated by a method of the present invention can be infused into the circulation. In the recipient that has undergone a myocardial infarct or is suffering from cardiac insufficiency or heart failure the enriched stem cell population can be infused directly into the coronary artery or applied directly to the injured heart tissue. Methods and compositions for administration of stem cells and enriched stem cell populations are known to the skilled artisan and are not considered part of the novelty of the present invention.

The following examples are provided merely as illustrative of various aspects of the invention and should not be construed to limit the invention in any way.

EXAMPLE 1

This example briefly describes the enrichment of a stem cell population from a sample of bone marrow collected from a normal donor. The bone marrow sample was treated with a shrinkage inducing agent prior to enrichment by tangential flow filtration. Briefly, 50 ml bone marrow was drawn from the hipbone of a normal volunteer, and 15 ml of phosphate buffered saline (PBS) supplemented with histamine was added to prevent clotting. After storage overnight, one third (about 33 ml) of this preparation was mixed with 33 ml of 30% dimethylsulfoxide (DMSO) in water. Following a 10 minute incubation at room temperature, 3 ml of a 25% solution of human serum albumin (HSA) was added and the mixture was loaded into the recirculation chamber of the tangential flow filtration device described briefly above, and more fully in U.S. provisional patent application Ser. No. 60/390,730, filed Jun. 19, 2002 and WO 2004/000444 (each incorporated herein by reference). Following two volume adjustments, the cells in the mixture were subjected to tangential flow filtration, with continuous replenishment of PBS with 0.625% HSA. At the end of the run, the cells were collected and analyzed. The preparation was found to be substantially clear of red blood cells and platelets. The percentage of CD34$^+$ cells increased from 4.78% to 18.2% of the total cell number, whereas the percentage of cells in the neutrophil gate as measured by fluorescent flow analysis decreased from 53.9% to 51.7%. The mean forward scatter of the cells in the neutrophil gate decreased from approximately 400 to approximately 250, indicating cell damage. The optimal method to date consisted of treating the bone marrow aspirate for 10-20 minutes with a mixture of DMSO and PBS followed by filtration on the TFF device for 60 minutes. The DMSO shock resulted in the shrinkage of the PMN's without collateral damage to the other cell populations present. The result was the concentration of the CD34$^+$/CD45$^+$ and CD133$^+$ cell population, while providing a reduced population of PMN cells, and lymphocytes. In one protocol bone marrow aspirate was treated with DMSO in diluted PBS for 20 minutes, followed by addition of human serum albumin (for stabilization of cells) and subsequent loading on the TFF device. The results can vary depending on the specific cell concentration of the input material. Two example runs are illustrated in Table I.

TABLE I

Characterization of cell preparation derived from bone marrow aspirate of two volunteers after concentration of stem cells on the TFF System

|  | RUN 1 | RUN 2 |
|---|---|---|
| Starting BM |  |  |
| CD34$^+$/45$^+$ | 5% | 4.2% |
| CD133$^+$/45$^-$ | not determined | 0.01% |
| PMN's | 74% | 66% |
| CD3 | 16% | 18% |
| After TFF RUN |  |  |
| CD34$^+$/45$^+$ | 18% | 13% |
| CD133$^+$/45$^-$ | not determined | 1.3% |
| PMN's | 53% | 53% |
| CD3 | 7% | 10% |

Table I shows a partial reduction in PMN's from as high as 74% initially to 53% due to reduction in cell size and removal by the TFF System. Enrichment of the CD34$^+$/45$^+$ cell population was from 5% to 18% in RUN 1 and from 4.2% to 13% in RUN 2. In addition there was a reduction of the lymphocyte population from 16% to 7% in RUN 1 and from 18% to 10% in RUN 2. The number of progenitor cells recovered was 11 million in RUN 1 and 16 million in RUN 2, far in excess of that recovered in clinical trials referenced here. These bone marrow-derived stem cells are capable of normal stem cell function in that colony forming assays have been carried out with vibrant colony formation in a short period of time. It should be noted that CD133$^+$ cells were also present in the isolated and concentrated stem cell population as illustrated in RUN 2, 0.1% being present in the starting material and 1.3% in the final preparation.

EXAMPLE 2

This example describes how a cell population enriched in stem cells as described above would be used to treat a patient that has had an acute myocardial infarct. Briefly, TFF purified stem cells from bone marrow are infused into the coronary artery of a patient that has undergone an acute myocardial infarct, following stent implantation. Subsequent remodeling of the cardiac muscle results in enhanced left ventricular end volume and reduced chance of dying from subsequent cardiac failure.

The examples are provided herein are intended to illustrate but not to limit the scope of the claimed invention. Other variants of the invention will be readily apparent to those of ordinary skill in the art and encompassed by the appended claims. All publications, patents, patent applications and other references cited herein and are also incorporated by reference herein.

What is claimed is:

1. A method for separating stem cells from a sample from a subject wherein the sample comprises stem cells and non-stem cell constituents wherein the non-stem cells constituents can include cell population which have essentially the same size as the stem cells, the method comprising separation on a tangential flow filtration device by:
   (i) pretreating the sample to induce cell shrinkage of cell populations with essentially the same size as the stem cells;
   (ii) introducing the sample into a remover unit (1) comprising a cross-flow chamber (3) through an inlet (6) in the remover unit;

(iii) subjecting the sample to cross-flow substantially parallel to a filter (5) having a pore size of about 1 to about 10 microns; and (iv) selectively removing non-stem cell constituents from the sample to form a cell population enriched for stem cells.

2. The method according to claim 1, further comprising:
preparing the sample from the subject by leukopheresis, density centrifugation, differential lysis, filtration, or preparation of a buffy coat, for introduction in the remover unit.

3. The method according to claim 1, wherein the sample is bone marrow, a tissue suspension, an organ suspension, or blood constituents.

4. The method according to claim 3, wherein the stem cells are hematopoietic stem cells, mesenchymal stem cells, or pluripotent stem cells.

5. The method according to claim 4, wherein the hematopoietic stem cells are $CD34^+$ cells.

6. The method according to claim 1, wherein the non-stem cell constituents are stroma, erythrocytes, plasma and platelets.

7. The method according to claim 1, further comprising repeating steps (i) and (ii) at least two times to form cell population enriched for stem cells.

8. The method according to claim 7, wherein the hematopoietic stem cells are $CD34^+$ cells.

9. The method according to claim 1, wherein the stem cells are hematopoietic stem cells, mesenchymal stem cells, or pluripotent stem cells.

10. The method according to claim 1, wherein the subject has undergone stem cell mobilization by administering a stem cell mobilization agent.

11. The method according to claim 10, wherein the stem cell mobilization agent is M-CSF, G-CSF, GM-CSF, or cyclophosphamide.

12. The method according to claim 1, wherein the tangential flow filtration device has a means for providing a predetermined input rate of the sample to the inlet of the cross-flow chamber; a means for controlling a filtration rate through the filter and into the filtrate chamber; and wherein the filtration rate controlling means limits the filtration rate to less than the unopposed filtration rate for the filter.

13. The method according to claim 1, wherein the cell population with essentially the same size are granulocytes.

14. The method according to claim 13, wherein granulocytes are preferentially removed from the cell mixture through lysis.

15. The method according to claim 14, wherein lysis is effected through sequential contact of the sample to an effective amount of DMSO and glycerol.

16. The method according to claim 15, wherein contact of the sample is with a solution with low osmotic strength.

17. The method according to claim 1, wherein the pretreatment comprises contacting the cells with a physiologically acceptable solution comprising dimethylsulfoxide (DMSO).

18. The method according to claim 17, wherein the final DMSO concentration is between 5% and 20%.

19. The method according to claim 18, wherein the final DMSO concentration is between 10% and 15%.

20. The method according to claim 19, wherein the final DMSO concentration is 12.5%.

21. The method according to claim 19, wherein the final DMSO concentration is 15%.

22. The method according to claim 17, wherein the physiologically acceptable solution is of low ionic strength.

23. The method according to claim 1, wherein the pretreatment comprises contacting the cells with a physiologically acceptable solution comprising glycerol.

24. The method according to claim 23, wherein the final glycerol concentration is between 0.5 mol/L and 2.5 mol/L.

25. The method according to claim 23, wherein the final glycerol concentration is 1 mol/L.

26. A method for enriching a sample of bone marrow or blood constituents for stem cells, comprising:

(i) pretreating the sample to induce cell shrinkage of cell populations with essentially the same size as the stem cells;

(ii) introducing the sample into a tangential flow filtration (TFF) unit, the TFF unit comprising a cross-flow chamber, a filtrate chamber, and a filter in fluid communication with the cross-flow chamber and the filtrate chamber, the filter having a pore size of about 1 to about 10 microns;

(iii) recirculating the sample through the TFF unit at a predetermined input rate and a predetermined filtration rate, the predetermined input rate at least five times the predetermined filtration rate; wherein the predetermined filtration rate is less than the unopposed filtration rate for the filter; and (iv) isolating a cell population enriched for stem cells.

27. The method according to claim 26, wherein the enriched cell population is substantially free of non-leukocyte blood constituents.

* * * * *